US006670445B2

(12) United States Patent
Okuhira

(10) Patent No.: US 6,670,445 B2
(45) Date of Patent: Dec. 30, 2003

(54) CURABLE COMPOUNDS, CURABLE RESIN COMPOSITIONS CONTAINING THE SAME AND METHODS OF EASILY DISASSEMBLING CURED MATERIALS

(75) Inventor: Hiroyuki Okuhira, Kanagawa (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

(21) Appl. No.: 10/109,686

(22) Filed: Apr. 1, 2002

(65) Prior Publication Data

US 2002/0183449 A1 Dec. 5, 2002

(30) Foreign Application Priority Data

Apr. 2, 2001 (JP) ......................................... 2001-102825

(51) Int. Cl.$^7$ ................................................... C08F 6/26
(52) U.S. Cl. ...................... 528/481; 156/344; 525/938; 528/33; 528/45; 528/76; 528/87; 528/374; 528/418
(58) Field of Search ............................ 525/938; 528/33, 528/76, 406, 481, 45, 67, 87, 354, 374, 418; 156/344

(56) References Cited

U.S. PATENT DOCUMENTS 5,973,033 A * 10/1999 Ober ........................... 523/443

FOREIGN PATENT DOCUMENTS

| JP | 10-025406 | 1/1998 |
| JP | 2850897 | 11/1998 |

* cited by examiner

Primary Examiner—Robert Dawson
Assistant Examiner—D. Aylward
(74) Attorney, Agent, or Firm—Rader Fishman & Grauer, PLLC

(57) ABSTRACT

Disclosed are a curable resin composition, which is liquid and therefore has good workability before curing and which can be softened or liquefied at a temperature lower than the thermal decomposition temperature in a short time after curing and a curable compound used in the composition as well as a method of easily disassembling a cured material. The curable compound has at least one thermally dissociable group (a) that does not participate in crosslinking reaction and at least two groups (b) participating in crosslinking reaction selected from the group consisting of an isocyanate group, a blocked isocyanate group, an alkoxysilyl group, an epoxy group, an acid anhydride group, an amino group, a latent amino group, a mercapto group and a carboxyl group.

11 Claims, No Drawings

CURABLE COMPOUNDS, CURABLE RESIN COMPOSITIONS CONTAINING THE SAME AND METHODS OF EASILY DISASSEMBLING CURED MATERIALS

BACKGROUND OF THE INVENTION

1. Field of the Invention

The present invention relates to curable compounds having in its molecular skeleton a group that is easily dissociated by heating after curing, curable resin compositions containing such compounds and methods of easily disassembling cured materials.

2. Description of the Related Art

In recent years, recycling properties are required in various fields in consideration of friendliness to the environment and a reduction in costs. Also, in the field of automobiles, disassembling of members bonded to each other with urethane adhesives has been being studied. This requires heating at 200° C. or more for softening or liquefying the urethane adhesives to thermally decompose the main chain and involves a problem of generating poisonous gas and the like. On the other hand, if thermoplastic adhesives are used, generation of poisonous gases upon disassembling is prevented. However, in this case a heating device is required at the time of coating so that the cost is high and the workability is poor. On the other hand, thermoplastic resin products have a disadvantage that since their softening starts at relatively low temperatures, their physical properties at high temperatures are poor so that they cannot be used at sites that will be exposed to high temperatures.

SUMMARY OF THE INVENTION

An object of the present invention is to provide a curable compound, a cured resin composition containing the curable compound, which is liquid and therefore has good workability before curing and which can be softened or liquefied at a temperature lower than the thermal decomposition temperature of the curable compound in a short time after curing as well as a method of easily disassembling a cured material therefrom.

The present inventors have made extensive studies on a curable resin composition that softens or liquefies at a temperature lower than its thermal decomposition temperature and a cured product can stably exist up to such a softening or liquefying temperature. As a result, they have found that by using a group that does not participate in crosslinking reaction and is dissociated above a temperature at which crosslinks are formed and below a temperature at which the bond formed by the crosslinking reaction or main chain is decomposed or dissociated, such as a hemiacetal ester group, and a group that participates in the crosslinking reaction, a resin composition having undergone curing can be liquefied or softened at a temperature lower than the temperature at which the bond formed by the crosslinking reaction or main chain is decomposed or dissociated in a short time. Thus, the present invention has been achieved.

Incidentally, it is known that the bond formed by hemiacetal esterification reaction between vinyl ether and a carboxylic acid is dissociated by heating and is stable at temperatures below the dissociation temperature (Chemical Abstract 43,6576d, 1949). Known technologies utilizing thermal dissociation of hemiacetal ester groups include a thermal latent curing agent which contains a carboxyl group-containing compound having a carboxyl group blocked and protected by hemiacetal ester reaction and which generates the carboxyl group by heating at the time of curing as disclosed in JP 2850897 B. However, no technology has been known yet which uses a compound having introduced in the skeleton thereof a hemiacetal ester group and being utilized for achieving recycling the resin from the cured product.

According to a first aspect of the present invention, there is provided a curable compound having at least one thermally dissociable group (a) and at least two groups (b) participating in crosslinking reaction. In a preferred embodiment, the curable compound has at least one thermally dissociable group (a) and at least two groups (b) participating in crosslinking reaction selected from the group consisting of an isocyanate group, a blocked isocyanate group, an alkoxysilyl group, an epoxy group, an acid anhydride group, an amino group, a latent amino group, a mercapto group and a carboxyl group.

Here, it is preferable that the thermally dissociable group (a) is a group represented by the following formula (1)

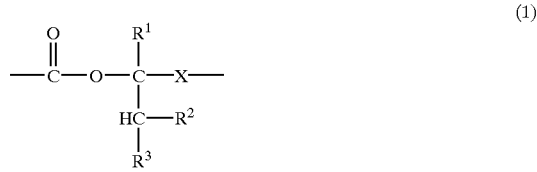

where $R^1$, $R^2$, and $R^3$ independently represent a hydrogen atom or a hydrocarbyl group having 1 to 18 carbon atoms and X represents an oxygen atom or a sulfur atom.

Also, it is preferable that the thermally dissociable group (a) is a hemiacetal ester group obtained by reaction between a carboxyl group and a vinyl ether group or a vinyl thioether group.

According to a second aspect of the present invention, there is provided a curable resin composition containing the curable compound.

According to a third aspect of the present invention, there is provided a method of easily disassembling a cured material, characterized by comprising heating a cured product obtained by curing the above-described composition to thermally dissociate the dissociable group (a) and to soften or liquefy the cured product.

Here, it is preferable that the group (b) participating in crosslinking reaction is selected from the group consisting of an isocyanate group, a blocked isocyanate group, an alkoxysilyl group, an epoxy group, an acid anhydride group, an amino group, a latent amino group, a mercapto group, a carboxyl group, an acrylate group and a hydroxyl group. It is more preferable that the crosslinking reactive group (b) is selected from the group consisting of an isocyanate group, a blocked isocyanate group, an epoxy group, an acid anhydride group, an amino group, a latent amino group and a carboxyl group.

It is preferable that the thermally dissociable group is a group represented by the following formula (1)

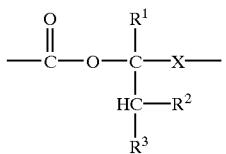

(1)

where R¹, R², and R³ independently represent a hydrogen atom or a hydrocarbyl group having 1 to 18 carbon atoms and X represents an oxygen atom or a sulfur atom.

It is preferable that the thermally dissociable group (a) is a hemiacetal ester group obtained by reaction between a carboxyl group and a vinyl ether group or a vinyl thioether group.

DETAILED DESCRIPTION OF THE PREFERRED EMBODIMENTS

Hereinafter, the present invention will be described in detail.

According to a first aspect of the present invention, there is provided a curable compound having at least one thermally dissociable group (a) and at least two groups (b) that participate in the crosslinking reaction selected from the group consisting of an isocyanate group, a blocked isocyanate group, an alkoxysilyl group, an epoxy group, an acid anhydride group, an amino group, a latent amino group, a mercapto group and a carboxyl group.

Here, the thermally dissociable group (a) means a group that does not participate in crosslinking reaction and is not dissociated at a temperature at which crosslinks are formed by the group (b) that participates in the crosslinking reaction but is dissociated at a temperature above a temperature at which crosslinks are formed and below a temperature at which the bond formed by the group (b) that participates in the crosslinking reaction or the main chain is decomposed or dissociated.

The thermally dissociable group (a) that the curable compound of the present invention has is not particularly limited as far as it is a group that is dissociated at a temperature above a temperature at which crosslinks are formed and below a temperature at which the bond formed by the crosslinking reaction or main chain is decomposed or dissociated as described above. Such groups preferably include those groups represented by the following formula (1).

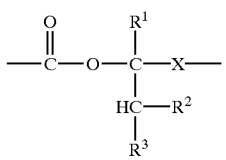

(1)

where R¹, R², and R³ independently represent a hydrogen atom or a hydrocarbyl group having 1 to 18 carbon atoms and X represents an oxygen atom or a sulfur atom.

The hydrocarbyl group having 1 to 18 carbon atoms represented by R¹, R², and R³ may be either one of an aliphatic hydrocarbyl group, an alicyclic hydrocarbyl group or an aromatic hydrocarbyl group. Among these, an aliphatic hydrocarbyl group is preferred.

Examples of the aliphatic hydrocarbyl group include a methyl group, an ethyl group, a n-propyl group, an isopropyl group, a n-butyl group, an isobutyl group, a 2,3-dimethylbutyl group, a s-butyl group, a t-butyl group, a pentyl group, an isoamyl group, a neopentyl group, a 4-methylpentyl group, a n-hexyl group, a 2-ethylhexyl group, an isohexyl group, a n-heptyl group, an isoheptyl group, a n-octyl group, an isooctyl group, a n-nonyl group, an isononyl group, a n-decyl group, an isodecyl group, a n-undecyl group, an isoundecyl group, a n-dodecyl group, an isododecyl group, a n-tridecyl group, an isotridecyl group, a n-tetradecyl group, an isotetradecyl group, a n-pentadecyl group, an isopentadecyl group, a n-hexadecyl group, an isohexadecyl group, a n-heptadecyl group, an isoheptadecyl group, a n-octadecyl group, an isooctadecyl group, a n-nonadecyl group, an isononadecyl group, a n-eicosyl group, an isoeicosyl group, etc. Lower alkyl groups including a methyl group, an ethyl group, a n-propyl group, an isopropyl group, a n-butyl group, an isobutyl group, a 2,3-dimethylbutyl group, a s-butyl group and a t-butyl group are preferably used.

Examples of the alicyclic hydrocarbyl group include a cyclopentyl group, a cyclohexyl group, a 1-cyclohexenyl group, a methylcyclohexyl group, a dimethylcyclohexyl group, a decahydronaphthyl group, a tricyclodecanyl group, etc.

Examples of the aromatic hydrocarbyl group include a phenyl group, an o-tolyl group, a p-tolyl group, a m-tolyl group, a 2,4-xylyl group, a mesityl group, a 1-naphthyl group, a benzyl group, a methylbenzyl group, β-phenylethyl group, a 1-phenylethyl group, a 1-methyl-1-phenylethyl group, a p-methylbenzyl group, a styryl group, a cinnamyl group, etc.

The hemiacetal ester groups represented by the formula (1) above can be obtained by the reaction between a carboxyl group and a vinyl ether group or vinyl thioether group and are stable at the crosslinking reaction temperature but are dissociated at temperatures lower than the thermal decomposition temperature of the cured product in a short time to give a carboxyl group and a vinyl ether group or vinyl thioether group.

The curable compound of the present invention has in its molecule at least two groups (b) participating in crosslinking reaction selected from the group consisting of an isocyanate group, a blocked isocyanate group, an alkoxysilyl group, an epoxy group, an acid anhydride group, an amino group, a latent amino group, a mercapto group and a carboxyl group, together with the thermally dissociable group (a) described above. Among these, an isocyanate group, a blocked isocyanate group, an epoxy group, an acid anhydride group, a latent amino group and carboxyl group are preferable.

Note that the at least two groups (b) that participate in the cross linking reaction may be the same or different from each other. It is preferred that the groups (b) that participate in the crosslinking reaction are present at terminals of the molecule.

Here, the blocked isocyanate group means a group derived from an isocyanate group that is blocked with a protecting group, which can be easily removed, for example, by heat to generate an isocyanate group. Preferred examples of the blocked isocyanate group include isocyanate groups blocked with blocking agents such as alcohols, phenols, oximes, triazoles, and caprolactams.

Preferred examples of the alcohols include methanol, ethanol, propanol, hexanol, lauryl alcohol, t-butanol, cyclohexanol, etc. Preferred examples of the phenols include xylenol, naphthol, 4-methyl-2,6-di-t-butylphenol, etc. Preferred examples of the oximes include 2,6-dimethyl-4-heptanoneoxime, methyl ethyl ketoxime, 2-heptanoneoxime, etc. Besides, 3,5-dimethylpyrazole, 1,2,4-triazole, etc. may be suitably used. Among these, methanol and xylenol are preferred as the blocking agent.

The latent amino group means an amino group that is blocked with a protecting group, which can be easily removed due to, for example, moisture or heat to generate an amino group. Examples thereof include ketimines, which are reaction products between an aliphatic polyamine and a ketone; boron trifluoride-amine complexes, which are compounds derived from an amine, such as n-hexylamine, monoethylamine, benzylamine, diethylamine, piperidine, triethylamine or aniline and boron trifluoride; dicyan diamide or derivatives of dicyan diamide such as o-tolylbiguanide, α-2,5-dimethylbiguanide, α,ω)-diphenylbiguanide, and 5-hydroxynaphthyl-1-biguanide; acid hydrazides such as succinohydrazide, adipohydrazide, isophthalohydrazide, p-oxybenzohydazide, and salicylohydrazide, phenylaminopropionohydrazide; diaminomaleonitrile or its derivatives; derivatives of melamine such as diallylmelamine; amineimides synthesized from a carboxylic acid ester, dimethylhydrazine and an epoxy compound; salts of a diamine such as ethylenediamine, hexamethylenediamine or piperidine with a dicarboxylic acid such as benzoic acid, phthalic acid, adipic acid or sebacic acid, salts of a polyamine such as 2,4,4-trimethyl-2,4,7-trihydroxyflavane with a polyhydroxyphenol such as N,N'-dimethyl-1,3-propanediamine, phenylphosphonic acid salts of polyamines, and phenylphosphoric acid salts of polyamines; and ester compounds of sulfonic acid with primary alcohols, monoesters or diesters of phosphoric acid or mixtures thereof, and ester compounds obtained by addition reaction between sulfonic acid and epoxy compounds. They also include ultraviolet absorbents such as aromatic diazonium salts and aromatic sulfonium salts.

The curable compounds of the present invention are compounds having introduced the thermally dissociable group (a) in the molecule having the above-described at least two groups (b) that participate in crosslinking reaction and being capable of forming crosslinking bonds.

In a case where the curable compound of the present invention is a low molecular weight compound that has the above-described thermally dissociable group (a) and the groups (b) that participate in crosslinking reaction, it forms crosslinking bonds with a resin component so that it can act as a curing agent.

Such a curable compound includes, for example, a compound obtained by the reaction between trimellitic anhydride with a compound having at least one of vinyl ether group and vinyl thioether group (hereinafter, referred to as "compound (c)").

Here, the compound (c) is not particularly limited but it is preferred that the vinyl ether group or vinyl thioether group is present at the terminal of the molecule and more preferably the compound (c) is a compound represented by the following formulae (2) or (3).

$$CH_2=CHO-Y-OCH=CH_2 \quad (2)$$

$$CH_2=CHS-Z-SCH=CH_2 \quad (3)$$

In the above formulae (2) or (3), Y and Z represent each a divalent hydrocarbyl group, which may be either straight chain or bonded with an alicyclic ring or an aromatic ring. Its molecular weight is not particularly limited. Specific examples thereof include 1,4-butanediol divinyl ether, nonanediol divinyl ether, cyclohexanediol divinyl ether, cyclohexanedimethanol divinyl ether, triethylene glycol divinyl ether, trimethylolpropane trivinyl ether, pentaerythritol tetravinyl ether, etc.

It is preferred that the carboxyl group of trimellitic anhydride and at least one of the vinyl ether group and vinyl thioether group of the compound (c) are reacted in amounts such that their molar ratio is approximately 1:1.

One preferred example of the curable compound of the present invention obtained by the reaction between trimellitic anhydride and the compound (c) includes the following acid anhydride A.

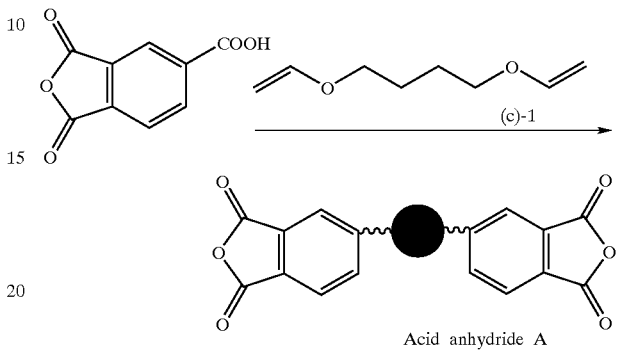

Acid anhydride A

In the above formula, the group represented by the symbol ● can be dissociated as shown below by heating at a temperature above the temperature at which crosslinking is formed.

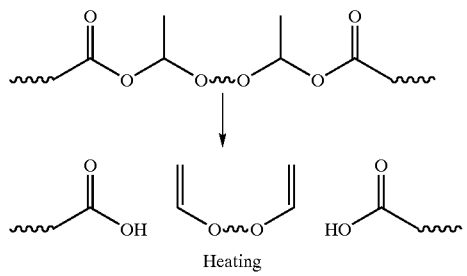

Heating

Examples of the resin component containing the curable compound having the above-described acid anhydride group and thermally dissociable group (a) as a curing agent include an epoxy resin.

Also, the above-described thermally dissociable group (a) may be introduced on the skeleton of a resin component. Such a resin component is not particularly limited as far as it is a thermosetting resin, and those compounds having introduced the group represented by the above-described formula (1) into the skeleton of, for example, a urethane prepolymer, epoxy resin or the like are suitable.

In a case where the group represented by the formula (1) above is introduced into the skeleton of a urethane prepolymer, the introduction may be performed by (i) reacting a polyol with methyl hexahydrophthalic anhydride or the like to synthesize a compound having at least one carboxyl group and at lest one hydroxyl group, (ii) reacting the at least one hydroxyl group with a polyisocyanate to obtain a compound having an isocyanate group and a carboxyl group (hereinafter, referred to as "compound (d)"), and (iii) then reacting the compound (d) with the above-described compound (c).

In the step (iii) above, the compound (d) and compound (c) may be used singly or two or more of them may be used in combination.

One preferred example of the curable compound of the present invention obtained by the reaction between the compound (d) and the compound (c) is the following urethane prepolymer A.

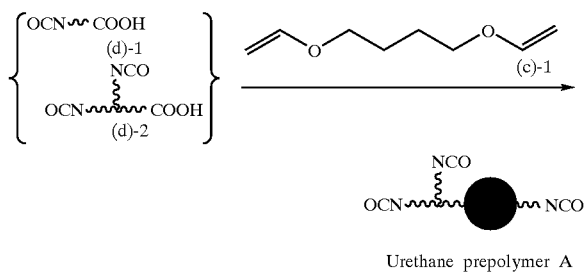

Urethane prepolymer A

In the above formula, the group represented by the symbol ● can be dissociated by heating at a temperature above the temperature at which crosslinking is formed as in the case of the above-described acid anhydride A.

Also, as shown in the following diagram, the urethane prepolymer A can be synthesized in a form where the compound (c) is omitted by introducing a carboxyl group into one of (d)-1 and (d)-2 and a vinyl ether group into the other.

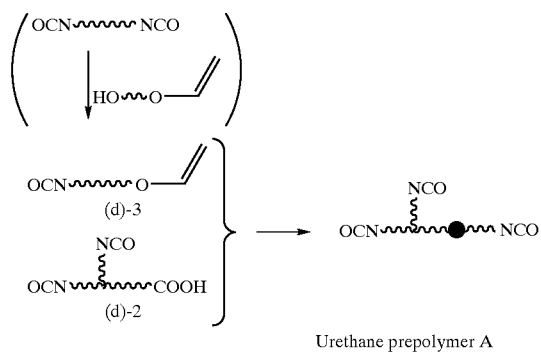

Urethane prepolymer A

The polyol used in the production of urethane prepolymer includes polyether polyols, polyester polyols, other polyols and mixed polyols containing mixtures thereof.

The polyether polyol includes polyether polyols obtained by adding one or more of propylene oxide, ethylene oxide, butylene oxide, styrene oxide and the like to one or more polyhydric alcohols such as ethylene glycol, diethylene glycol, propylene glycol, dipropylene glycol, glycerol, 1,1,1-trimethylolpropane, 1,2,5-hexanetriol, 1,3-butanediol, 1,4-butanediol, 4,4'-dihydroxyphenylpropane, 4,4'-dihydroxyphenylmethane, and pentaerythritol.

The polyester polyol includes condensation polymers between one or more of ethylene glycol, propylene glycol, butanediol, pentanediol, hexanediol, cyclohexanedimethanol, glycerol, 1,1,1-trimethylolpropane and the like low molecular weight polyols and one or more of glutaric acid, adipic acid, pimelic acid, suberic acid, sebacic acid, terephthalic acid, isophthalic acid and the like low molecular weight carboxylic acids or one or more oligomers; ring opening polymers such as propionolactone, valerolactone and caprolactone.

Other polyols include polymer polyols, polycarbonate polyols, polybutadiene polyols, hydrogenated polybutadiene polyols, acrylic polyols, and low molecular weight polyols such as ethylene glycol, diethylene glycol, propylene glycol, dipropylene glycol, butanediol, pentanediol and hexanediol, etc.

The polyisocyanate is not particularly limited as far as it is a compound that contains two or more isocyanate groups and specific examples thereof include aromatic polyisocyanates such as 2,4-tolylene diisocyanate (2,4-TDI), 2,6-tolylene diisocyanate (2,6-TDI), 4,4'-diphenylmethane diisocyanate (4,4'-MDI), 2,4'-diphenylmethane diisocyanate (2,4'-MDI), p-phenylene diisocyanate, polymethylene polyphenylene polyisocyanate, xylylene diisocyanate (XDI), and 1,5-naphthalene diisocyanate; aliphatic polyisocyanates such as hexamethylene diisocyanate (HDI), and norbornane diisocyanate (NBDI); alicyclic polyisocyanates such as isophorone diisocyanate (IPDI), $H_6XDI$ (hydrogenated XDI), and $H_{12}MDI$ (hydrogenated MDI); carbodiimide-modified polyisocyanates derived from the above-described polyisocyanates, or isocyanurate-modified polyisocyanates derived therefrom and so forth.

Also, isocyanate compounds having at least one isocyanate group having a great steric hindrance may be used. Specific examples include preferably TMI (monoisocyanate compound) produced by Mitsui Cytec, Ltd., TMXDI (diisocyanate compound), Saisen (triisocyanate compound) and the like. These may be used singly or two or more of them may be used in combination.

The urethane polymer having introduced therein the thermally dissociable group (a) can form crosslinking bonds with moisture or a curing agent commonly used for urethane-based compositions. The curing agent includes preferably latent curing agents, e.g., polyamines, polythiols, polyols and the like as well as ketimines (including enamines), which are reaction products between a polyamine and a carbonyl compound, oxazolidines, which are reaction products between an amino alcohol and a carbonyl compound.

The thermally dissociable group includes, in addition to groups generated by reaction between a carboxyl group and a vinyl ether group or vinyl thioether group, those groups generated by reactions of an acid anhydride group with a hydroxyl group, a halogenated alkyl group with a tertiary amino group, an isocyanate group with a phenolic hydroxyl group, and an azlactone group with a phenolic hydroxyl group or a functional group generated by dimerization reaction of a nitroso group and the like.

According to a second aspect of the present invention, there is provided a curing resin composition containing the above-described curable compound (hereinafter, referred to as "composition of the present invention").

In the composition of the present invention, the curable compound of the present invention may be either a resin component or a curing agent component. Preferred examples of the composition of the present invention include the following.

(1) Epoxy Resin Compositions

In a case where a compound having an acid anhydride group and a hemiacetal group is used as the curable compound of the present invention, the resin component includes an epoxy resin that can form crosslinking with the acid anhydride group.

The epoxy resin includes, for example, bisphenol A epoxy resins, bisphenol F epoxy resins, bisphenol S epoxy resins, biphenyl epoxy resins, naphthalene epoxy resins, novolak epoxy resins, epoxy resins having a fluorene skeleton, epoxy resins made from a copolymer of a phenol compound and dicyclopentadiene as a raw material, glycidylamine epoxy resins such as diglycidyl resorcinol, tetrakis(glycidyloxyphenyl)ethane, tris(glycidyloxyphenyl)methane, tris(glycidylamino)phenol, tris(glycidylamino)cresol, and tetraglycidylxylenediamine, and alicyclic epoxy resins such as vinylcyclohexene diepoxide. These may be used singly or two or more of them may be used in combination. Among these, bisphenol A epoxy resins are suitable in consideration of particularly excellent adhesive property.

(2) Urethane Prepolymer Compositions

In a case where the urethane prepolymer having introduced the thermally dissociable group (a) into the skeleton as the curable compound of the present invention, the urethane composition can cure with moisture only. Also, it may contain a compound commonly used for urethane prepolymer compositions having a hydroxyl group, a mercapto group and a latent amino group that can form crosslinking with the isocyanate groups of the urethane prepolymer.

It is preferred that the composition contains latent curing agents such as ketimines (including enamines), which are reaction products of a polyamine and a carbonyl compound, oxazolidines, which are reaction products of an amino alcohol and a carbonyl compound. The components of the curing agent may be used singly or two or more of them may be used in combination.

The ketimines used in the composition of the present invention are not particularly limited as far as they are reaction products between a polyamine and a carbonyl compound. The carbonyl compound used for the synthesis of ketimines preferably includes carbonyl compounds having a substituent at the α-position of carbonyl carbons and having a great steric hindrance from a point of view of giving good storage stability. The carbonyl compound having a substituent at the α-position of carbonyl carbons is a carbonyl compound having a substituent at the α-position counting from the carbonyl group. Examples of such a carbonyl compound include those compounds represented by the following formula (4)

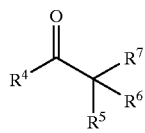

(4)

where $R^4$ represents a hydrogen atom or a methyl group, $R^5$ represents an alkyl group having 1 to 6 carbon atoms, $R^6$ represents a methyl group or an ethyl group, and $R^7$ represents a hydrogen atom, a methyl group or an ethyl group.

Here, the alkyl group having 1 to 6 carbon atoms represented by $R^5$ include, for example, a methyl group, an ethyl group, a propyl group, a butyl group, a pentyl group, a hexyl group, etc. Further, $R^5$ and $R^6$ may combine to form a cyclohexyl ring. Specifically, preferred examples of the above-described carbonyl compound include methyl isopropyl ketone (MIPK), methyl t-butyl ketone (MTBK), and methyl cyclohexyl ketone.

The polyamine used for the synthesis of the ketimines is not particularly limited but aliphatic polyamines are preferred in consideration of high curing rates.

Examples thereof include 2,5-dimethyl-2,5-hexamethylenediamine, methenediamine, 1,4-bis(2-amino-2-methylpropyl)piperazine, polypropylene glycol (PPG) having an amino group bonded to each of the propylene branching carbon at the both terminals of the molecule (for example, Jefermin D230®, Jefermin D400®, etc., produced by Sun Techno Chemical, Co., Ltd.), diamines having a polyether skeleton having a methylene group bonded to the amine nitrogen, such as ethylenediamine, propylenediamine, butylenediamine, diethylenetriamine, triethylenetetramine, tetraethylenepentamine, pentaethylenehexamine, hexamethylenediamine, trimethylhexamethylenediamine, N-aminoethylpiperazine, 1,2-diaminopropane, iminobispropylamine, methyliminobispropylamine, and $H_2N(CH_2CH_2O)_2(CH_2)_2NH_2$ (Jefermin EDR148®, produced by Sun Techno Chemical Co., Ltd.), 1,5-diamino-2-methylpentane (MPMD produced by DuPont Japan Co., Ltd.), metaxylylenediamine (MXDA), polyamideamine (X2000 produced by Sanwa Chemical Co., Ltd.), isophoronediamine, 1,3-bisaminomethylcyclohexane (1,3BAC, produced by Mitsubishi Gas Chemical Company, Inc.), 1-cyclohexylamino-3-aminopropane, 3-aminomethyl-3,3,5-trimethylcyclohexylamine, dimethyleneamine having a norbornane skeleton (NBDA produced by Mitsui Chemical, Inc.), etc. Among these, 1,3BAC, NBDA, MXDA, Jefermin EDR148®, and polyamideamine are preferred.

The ketimines suitably used from the viewpoint of elevating storage stability and curability of the composition of the present invention include those obtained from MIPK or MTBK and Jefermin EDR148®, those obtained from MIPK or MTBK and 1,3BAC, those obtained from MIPK or MTBK and NBDA, those obtained from MIPK or MTBK and MXDA, and those obtained from MIPK or MTBK and X2000, and the like.

Among these, in particular those obtained from MIPK or MTBK and NBDA or 1,3BAC are preferred since they exhibit excellent curability. Furthermore, those obtained from MIPK or MTBK and X2000 are preferred since they exhibit excellent adhesive property to wet surface.

The above-described ketimines can be obtained by reaction by heating under reflux the above-described carbonyl compound and polyamine in the absence of solvents or in the presence of a solvent such as benzene, toluene or xylene and removing eliminated water by means of azeotropy.

It is preferred that the ketimines are used in amounts such that the molar ratio of (isocyanate group in the resin component)/(ketimine group in the ketimines) is from 0.5 to 100, more preferably from 0.8 to 50.

The oxazolidines used in the composition of the present invention are not particularly limited as far as they are reaction products between an amino alcohol and a carbonyl compound. The carbonyl compound used in the synthesis of oxazolidines may include the above-described carbonyl compounds suitably used for the synthesis of the ketimines from the viewpoint of providing good storage stability.

The amino alcohol used for the synthesis of oxazolidines is not particularly limited and preferred examples thereof include N-methylethanolamine, N-ethylethanolamine, N-propylethanolamine, N-butylethanolamine, N-t-butylethanolamine, 2-hydroxyethylamine, 1-amino-2-propanol, N-(2-hydroxyethyl)-N-(2-hydroxypropyl)amine, bis-N-(2-hydroxyethyl)amine, N-(2-aminoethyl) ethanolamine, N-(2-aminoethyl) isopropanolamine, etc. N-methylethanolamine, N-ethylethanolamine, bis-N-2-hydroxyetylamine and the like are suitable in consideration of curing rate and price.

Examples of oxazolidines that can be suitably used include those obtained by those obtained from MIPK or MTBK and N-methylethanolamine or N-ethylethanolamine from the viewpoint of elevating storage stability and curability of the composition of the present invention.

The oxazolidines can be obtained by reaction by heating under reflux a carbonyl compound and an amino alcohol in the absence of solvents or in the presence of a solvent such as benzene, toluene or xylene and removing eliminated water by means of azeotropy.

It is preferred that the oxazolidines are used in amounts such that the molar ratio of (isocyanate group in the resin component)/(oxazolidinyl group in the oxazolidines) is from 0.5 to 100, more preferably from 0.8 to 50.

The composition of the present invention may further contain additives such as fillers, curing auxiliaries, antioxidants, solvents, and plasticizers.

The production method for the composition of the present invention is not particularly limited and the composition of the present invention is produced by sufficiently mixing and kneading a resin component and a curing agent component with optionally adding the above-described additives as necessary under reduced pressure and uniformly dispersing each component.

The composition of the present invention can be softened or liquefied by heating at a relatively low temperature in a short time after it is cured by crosslinking reaction and in addition, the cured product is stable at temperatures below that temperature. Therefore, the composition of the present invention can be suitably used as an adhesive or sealing agent in the fields of automobile as well as civil engineering and building construction. The members bonded to each other with the composition of the present invention can be disassembled without difficulty by heating.

According to a third aspect of the present invention, there is provided a method of easily disassembling a cured material, comprising crosslinking a prepolymer composition having a crosslinking reactive group and a thermally dissociable group and heating a cured product to dissociate the thermally dissociable group thereby softening or liquefying the cured product.

It is preferred that the crosslinking reactive group is selected from the group consisting of an isocyanate group, a blocked isocyanate group, an alkoxysilyl group, an epoxy group, an acid anhydride group, an amino group, a latent amino group, a mercapto group, a carboxyl group, an acrylate group, and a hydroxyl group. Among these, an isocyanate group, a blocked isocyanate group, an epoxy group, an acid anhydride group and a latent amino group are more preferable.

The thermally dissociable group means a group that is not dissociated at the temperature at which crosslinks are formed by the crosslinking reactive groups but is dissociated at a temperature above a temperature at which crosslinks are formed and below a temperature at which the bond formed by the crosslinking reactive group or main chain is decomposed or dissociated. It is preferred that the thermally dissociable group is a group represented by the above-described formula (1) and more preferably a hemiacetal ester group obtained by reaction between a carboxyl group and a vinyl ether group or vinyl thioether group.

The prepolymer composition having the above-described crosslinking reactive group and thermally dissociable group is not particularly limited and suitable examples thereof include the above-exemplified epoxy resin compositions and urethane prepolymer compositions, which are suitably used as adhesives for bonding various members to each other. Note that the members as used herein include also reinforcing wires.

According to the third embodiment of the present invention, cured materials, which are complexes of members obtained by curing these prepolymer compositions and cured products, can be disassembled at temperatures lower than the thermal decomposition temperature of the cured products.

For example, a cured material made of members bonded to each other with an epoxy resin composition can be easily disassembled by heating the cured material at a temperature above the temperature at which crosslinks are formed and below the temperature at which the bond formed by the crosslinking reactive group or the main chain is decomposed or dissociated to soften the cured product. More specifically, by heating a cured material, which was obtained by standing at about 130° C. for about 20 hours at about 180° C. for 15 minutes, the cured product can be easily disintegrated with a spatula or the like.

Furthermore, a cured material made of members bonded to each other with a crosslinked urethane prepolymer composition can be easily disassembled by heating the cured product in a similar manner to liquefy the cured product. More specifically, by heating the cured material, which was aged at 20° C. and at a humidity of 60% for 1 week, at 170° C. for 5 minutes, the cured product is liquefied and the members bonded to each other can be easily removed.

By this method, cured materials can be disassembled at a temperature lower than the thermal decomposition temperature in a short time and in addition, the method involves no generation of poisonous gases upon disassembling the cured material so that recycling of the members becomes easy and the members can be easily removed also from the reinforcing members.

EXAMPLES

Hereinafter, the present invention will be explained in more detail by way of examples. However, the present invention should not be limited to the following examples.

Examples 1 to 4 and Comparative Examples 1 and 2

Urethane prepolymers, an epoxy resin, a ketimine, a norbornane diamine and acid anhydrides were mixed to prepare compositions having the composition ratios shown in Table 1, and the obtained compositions were evaluated for their easy disassembling property by the following method.

[1] Urethane Prepolymer A

After mixing 453 g of a diol having a number average molecular weight of 2,000 (Exenol 2020®; Asahi Glass Company, Ltd.) and 37.5 g of a monofunctional acid anhydride (B650; produced by Dainippon Ink and Chemicals, Inc.), the mixture was stirred at 120° C. for 24 hours and PPG (a) having a hydroxyl group and a carboxyl group in the molecule was obtained. 345 g of a triol having a number average molecular weight of 3,000 (Exenol 3030; Asahi Glass Company, Ltd.) and 12.6 g of an acid anhydride (B650) were reacted at 120° C. for 24 hours to obtain PPG (b) having two hydroxyl groups and one carboxyl group in the molecule.

Then, 50 g of PPG (a) (carboxyl group; 22.7 mmol), 71.2 g of PPG (b) (carboxyl group; 22.7 mmol) and 16.7 g of TMXDI (NCO/OH=2.0) (produced by Mitsui Cytech, Ltd.) were mixed and then reacted at 100° C. for 10 hours.

Thereafter, butanediol divinyl ether was mixed at a molar ratio of (carboxyl group/vinyl ether group)=1.0 and reaction was performed at 100° C. for 10 hours in the presence of acidic phosphoric acid ester catalyst to obtain urethane prepolymer A having a number average molecular weight of 5,000 and NCO%=2.2%.

[2] Urethane Pepolymer B

Urethane prepolymer B having a number average molecular weight of 5,000 and NCO%=2.2% was obtained in the manner as urethane prepolymer A except that TMXDI was replaced by TDI (Cosmonate T-80®; produced by Mitsui Chemical, Inc.).

[3] Urethane Prepolymer C

The urethane prepolymer A and methyl ethyl ketone oxime were mixed in amounts such that the equivalent ratio of NCO/oxime was 1 and stirred at 80° C. for 20 hours to obtain urethane prepolymer C having blocked isocyanate group.

[4] Urethane Prepolymer D

A trifunctional polypropylene glycol having a number average molecular weight of 5,000 (Exenol 5030®; produced by Asahi Glass Company, Ltd.) and TMXDI were mixed in amounts such that the molar ratio of NCO/OH was 2.0 and stirred at 80° C. for 8 hours in the presence of a tin catalyst to obtain urethane prepolymer D having a number average molecular weight of 5,000 and NCO%=2.1%.

[5] Epoxy Resin

Commercially available bisphenol A type epoxy resin (EP4100E, produced by Asahi Denka Kogyo K.K.) was used.

[6] Ketimine 100 g of norbornanediamine (NBDA, produced by Mitsui Chemical, Inc.) and 167 g of methyl isopropyl ketone (MIPK) together with 200 g of toluene were charged in a flask and reaction was performed for 20 hours while removing produced water by azeotropy. Thereafter, toluene and excessive MIPK were removed by distillation to obtain the objective ketimine.

[7] Acid Anhydride A

Trimellitic anhydride and 1,4-butanediol divinyl ether were mixed in amounts such that the molar ratio of COOH/(CH$_2$=CHO) was 1.0 and the mixture was stirred at 70° C. for 3 hours in the presence of an acid phosphoric acid ester as catalyst to obtain a compound, which was pulverized to obtain acid anhydride A.

[8] Acid Anhydride B

Commercially available ethylene glycol type acid anhydride (Rikacid TMEG®; New Japan Chemical K. K.) was used.

Evaluation of Easy Disassembling Property (1) Urethane Prepolymer Compositions

After heating cured products (sheets), which were obtained by aging the compositions under the conditions of 20° C. and a humidity of 60% for 1 week, at 180° C. for 15 minutes, the liquefying state of the sheets was visually observed, and those liquefied and flown were evaluated as O and those that retained their shape were evaluated as X.

Epoxy Resin Compositions

After heating cured products, which were obtained by standing the compositions under the conditions of 130° C. for 20 hours, at 170° C. for 5 minutes, the sheets were compressed at 4 MPa and their state was observed, and those destroyed were evaluated as O and those that retained their shape were evaluated as X.

TABLE 1

Unit of component: part by weight

| | Urethane prepolymer | | | | Epoxy resin | |
| --- | --- | --- | --- | --- | --- | --- |
| | Example 1 | Example 2 | Example 3 | Comparative Example 1 | Example 4 | Comparative Example 2 |
| Urethane prepolymer A | 100 | 0 | 0 | 0 | 0 | 0 |
| Urethane prepolymer B | 0 | 100 | 0 | 0 | 0 | 0 |
| Urethane prepolymer C | 0 | 0 | 100 | 0 | 0 | 0 |
| Urethane prepolymer D | 0 | 0 | 0 | 100 | 0 | 0 |
| Epoxy resin | 0 | 0 | 0 | 0 | 100 | 100 |
| Ketimine | 7.1 | 0 | 0 | 6.8 | 0 | 0 |
| Norbornane diamine | 0 | 0 | 4 | 0 | 0 | 0 |
| Acid anhydride A | 0 | 0 | 0 | 0 | 65 | 0 |
| Acid anhydride B | 0 | 0 | 0 | 0 | 0 | 65 |
| Easy disassembling property | O | O | O | X | O | X |

As will be apparent from Table 1, the composition containing a compound having introduced the thermally dissociable group (a) in the molecular skeleton thereof can be easily disassembled by additionally applying heat thereto after curing.

According to the present invention, a curable resin composition, which is liquid and therefore has good workability before curing and that can be softened or liquefied at a temperature lower than the thermal decomposition temperature in a short time after curing and a curable compound used in the composition as well as a method of easily disassembling the cured material are provided. The cured material bonded with the curable resin composition of the present invention causes no problem of generation of poisonous gases and can be easily disassembled.

What is claimed is:

1. A curable compound having at least one thermally dissociable group (a) that does not participate in a crosslinking reaction and is dissociated above a temperature at which crosslinks are formed and below a temperature at which a bond formed by the crosslinking reaction or main chain is decomposed or dissociated, and at least two groups (b) participating in crosslinking reaction.

2. A curable compound according to claim 1, wherein the curable compound has at least one thermally dissociable group (a) and at least two groups (b) participating in crosslinking reaction selected from the group consisting of an isocyanate group, a blocked isocyanate group, and alkoxysilyl group, an epoxy group, an acid anhydride group, an amino group, a latent amino group, a mercapto group and a carboxyl group.

3. A curable compound according to claim 2, wherein the thermally dissociable group (a) is a group represented by the following formula (1)

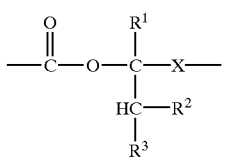
(1)

where $R_1$, $R_2$, and $R_3$ independently represent a hydrogen atom or a hydroxyl group having 1 to 18 carbon atoms and X represents an oxygen atom or a sulfur atom.

4. A curable compound according to claim 3, wherein the thermally dissociable group (a) is a hemiacetal ester group obtained by reaction between a carboxyl group and a vinyl ether group or a vinyl thioether group.

5. A curable compound according to claim 2, wherein the groups (b) are selected from the group consisting of an isocyanate group, a blocked isocyanate group, an epoxy group, an acid anhydride group and a latent amino group.

6. A curable resin composition comprising the curable compound as claimed in any one of claims 1 to 5.

7. A method of easily disassembling a cured material, comprising heating a cured product obtained by curing a curable resin composition comprising a curable compound having at least one thermally dissociable group (a) and at least two groups (b) participating in crosslinking reaction, said heating being performed to thermally dissociate the thermally dissociable group (a) thereby softening or liquefying the cured product.

8. A method of easily disassembling a cured material according to claim 7, wherein the curable compound has at least one thermally dissociable group (a) and at least two groups (b) participating in crosslinking reaction selected from the group consisting of an isocyanate group, a blocked isocyanate group, and alkoxysilyl group, an epoxy group, an acid anhydride group, an amino group, a latent amino group, a mercapto group a carboxyl group, an acrylate group and a hydroxyl group.

9. A method of easily disassembling a cured material according to claim 7, wherein the crosslinking reactive group is selected from the group consisting of an isocyanate group, a blocked isocyanate group, an epoxy group, an acid anhydride group, a latent amino group, an acrylate group and a hydroxyl group.

10. A method of easily disassembling a cured material according to claim 7, wherein the thermally dissociable group is a group represented by the following formula (1)

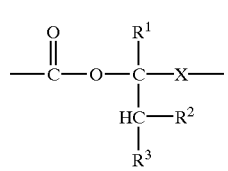
(1)

where $R_1$, $R_2$, and $R_3$ independently represent a hydrogen atom or a hydroxyl group having 1 to 18 carbon atoms and X represents an oxygen atom or a sulfur atom.

11. A method of easily disassembling a cured material according to claim 10, wherein the thermally dissociable group (a) is a hemiacetal ester group obtained by reaction between a carboxyl group and a vinyl ether group or a vinyl thioether group.

\* \* \* \* \*